US00PP07956P

United States Patent [19]

Alston

[11] Patent Number: Plant 7,956

[45] Date of Patent: Sep. 1, 1992

[54] APPLE TREE — FIESTA CULTIVAR

[75] Inventor: Frank H. Alston, Maidstone, England

[73] Assignee: Plant Breeding International Cambridge Limited, Cambridge, United Kingdom

[21] Appl. No.: 639,271

[22] Filed: Dec. 24, 1990

[51] Int. Cl.[5] ..... A01H 5/00
[52] U.S. Cl. ..... Plt./34.1
[58] Field of Search ..... Plt. 34

*Primary Examiner*—James R. Feyrer
*Attorney, Agent, or Firm*—Burns, Doane, Swecker & Mathis

[57] ABSTRACT

A new and distinct variety of high yielding dessert apple tree is provided which originated as a cross between the Cox's Orange Pippin cultivar and the Idared cultivar. The fruit is an attractive bright red on a yellow-green background, possesses an excellent flavor, and exhibits an extended storage life. The growth habit is precocious and leads to the formation of a tree which is larger in size than Cox's Orange Pippin. The branches form wide angles and commonly are drooping particularly on young trees. The fruit skin finish is superior and of a brighter coloration than that of Cox's Orange Pippin cultivar.

3 Drawing Sheets

SUMMARY OF THE INVENTION

The new cultivar of dessert apple tree was created by pollination wherein two parents were crossed which previously had been studied in the hope that they would contribute the desired characteristics. The resulting family of seedlings was germinated during 1973 at the East Malling Research Station of the Kent Incorporated Society for Promoting Experiments in Horticulture, East Malling, Maidstone, Kent, ME19 6BJ, England (now Horticulture Research International) where subsequent selection was carried out. The female parent (i.e., the seed parent) of the new cultivar was the Cox's Orange Pippin cultivar (nonpatented in the United States). The Male parent (i.e., the pollen parent) of the new cultivar was the Idared cultivar (nonpatented in the United States). The Idared cultivar was formed by crossing the Jonathan and Wagener cultivars and was introduced during 1942 by the Idaho Agricultural Experiment Station, Moscow, Id. The parentage of the new cultivar can be summarized as follows:

COX'S ORANGE PIPPIN×IDARED.

The seeds resulting from the above pollination were sown and plants were obtained which were physically and biologically different from each other. Selective study has resulted in the identification of a single plant of the new cultivar.

It was found that the new cultivar of dessert apple tree possesses the following combination of characteristiscs:

(a) is precocious and assumes a larger size than the Cox's Orange Pippin cultivar,
(b) exhibits a somewhat drooping growth habit which is particularly noticeable in young trees,
(c) forms in good yields attractive round and slightly flattened fruit having a smooth and shiny surface with a bright red blush which may be present as stripes and speckles on a yellow-green background and possessing an excellent flavor which is well retained upon storage, and (d) commonly exhibits a genetic leaf mottle which is unrelated to disease.

The new cultivar has been found to perform well on dwarfing rootstocks, such as M9 and M27, and on semidwarfing rootstocks such as MM106. When the new cultivar is grown on MM106 rootstock, the resulting trees of the new cultivar commonly are approximately twenty-five percent larger than those of the Cox's Orange Pippin cultivar. It is not recommended that trees of the new cultivar be grown on their own roots.

The fruit of the new cultivar is superior to that of each of its parents. The fruit exhibits a brighter red overall appearance than the Cox's Orange Pippin cultivar and the skin finish is considerably more attractive. More specifically, the skin finish of the Cox's Orange Pippin cultivar commonly is at least partially russetted while the skin finish of the new cultivar commonly bears little or no russet and is smooth and shiny without undue greasiness at the time of harvest.

The extent of the red fruit coloration is influenced by the level of exposure to direct sunlight and commonly covers approximately fifty percent of the skin surface.

The fruit of the new cultivar exhibits a sweet but tart flavor with a pleasant aromatic taste. The fruit also has been demonstrated to exhibit significantly improved storage characteristics with good retention of fruit quality which exceeds the storage life of the Cox's Orange Pippin cultivar. For instance, the fruit of the new cultivar can be stored in air at 3.5° C. until January, and until June when stored in controlled atmosphere of <1 percent carbon dioxide and 1.25 percent oxygen. Accordingly, the fruit of the new cultivar is expected to compete favorably in the marketplace during May and June with fruit importations from the southern hemisphere.

The new cultivar has been found to fall within pollination Group No. 3 together with the Cox's Orange Pippin, Jonathan, and Wagener cultivars. The new cultivar commonly flowers approximately two days later than the Cox's Orange pippin cultivar. It is favorable to pollen from Gala, Katy, Golden Delicious, and most any compatible diploid which produces pollen at the appropriate time. The new cultivar has exhibited a slight tendency to self-fertility. Additionally, its styles have been demonstrated to be somewhat more receptive to pollen at lower temperatures than those the Cox's Orange Pippin parent. Preliminary testing has suggested that the new cultivar may not be a good pollinator for Cox's Orange Pippin.

No significant physiological disorders are known for the new cultivar. Slight fruit storage disorders have been noted occasionally and manganese toxicity has been observed in some nursery trees of the new cultivar. It has been found to be susceptible to European canker, mildew, and scab. However, these can be readily controlled through the use of conventional spray programs.

The performance of the new cultivar has been evaluated at the East Malling Research Station; the National Fruit Trials at Faversham, Kent, ME13 8XZ, England; and elsewhere in the United Kingdom and Europe.

The new cultivar has been propagated using virus-indexed material by budding, grafting, etc., onto appropriate rootstocks. The characteristics of the new cultivar have been found to be stable and to be capable of transmission through succeeding generations by such asexual propagation.

The new cultivar initially was designated T31/31, and subsequently has been named the FIESTA cultivar.

BRIEF DESCRIPTION OF THE PHOTOGRAPHS

The accompanying photographs show typical specimens of the new variety as depicted in color as nearly true as it is reasonably possible to make the same in color illustrations of this character. The photographs were taken during the month of September. FIGS. 1 and 2 were obtained during 1983 at the National Fruit Trials, Faversham, Kent, England.

FIG. 1 illustrates a four to five year-old tree of the new cultivar and shows the typical drooping growth habit and the distribution of the fruit.

FIG. 2 illustrates a closer view of the typical fruit of the new cultivar during the course of ripening while present on the tree. It will be noted that those portions of the fruit which are in full sun generally assume more of the overlying red coloration. Also, the typical green-yellow mottling is visible on some of the leaves which is not the result of a virus infection.

FIG. 3 illustrates five typical ripe fruits of the new cultivar.

DETAILED DESCRIPTION

The following is a detailed description of the new cultivar. The specimens described were grown at the Brogdale Experimental Horticulture Station, Faversham, Kent, ME13 8XZ, England. The chart used in the identification of colors is that of The Royal Horticultural Society (R.H.S. Colour Chart).

Figure 1:
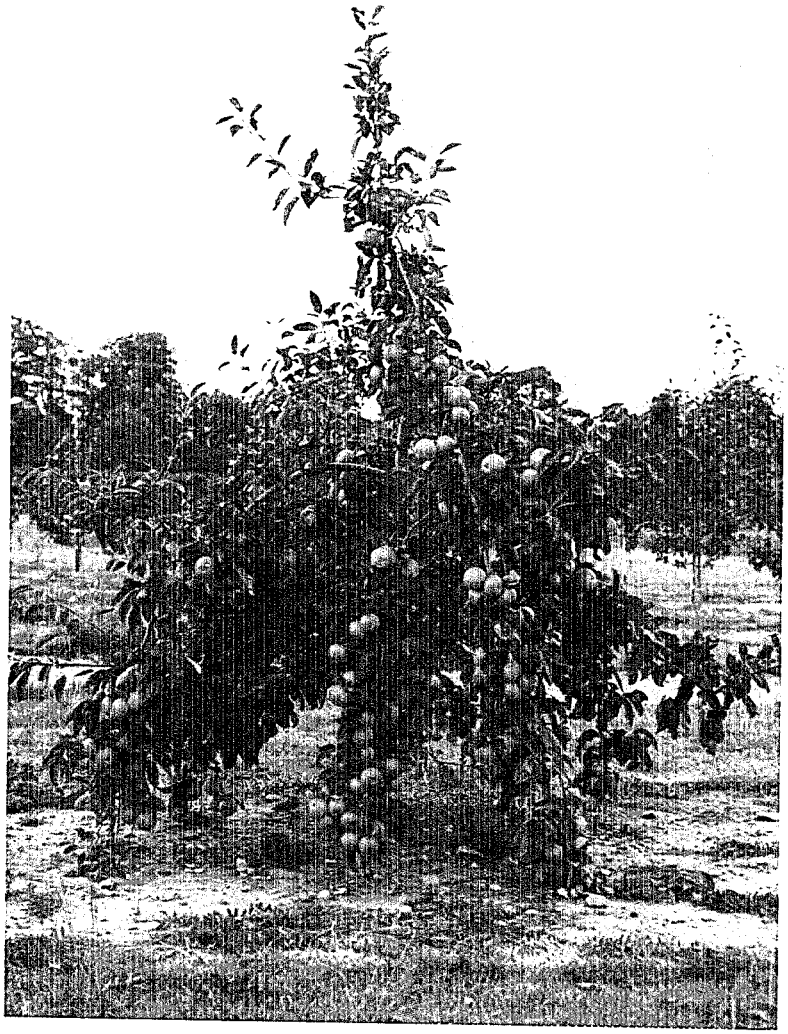
Figure 2:
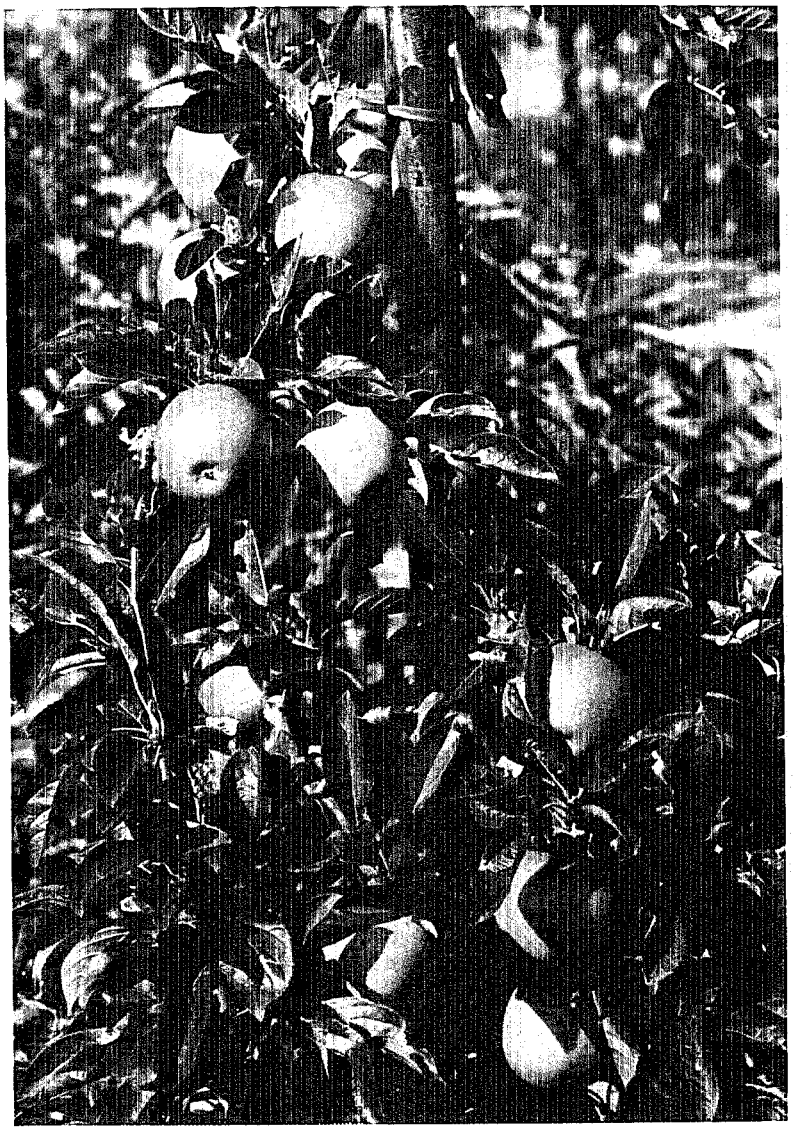
Figure 3:
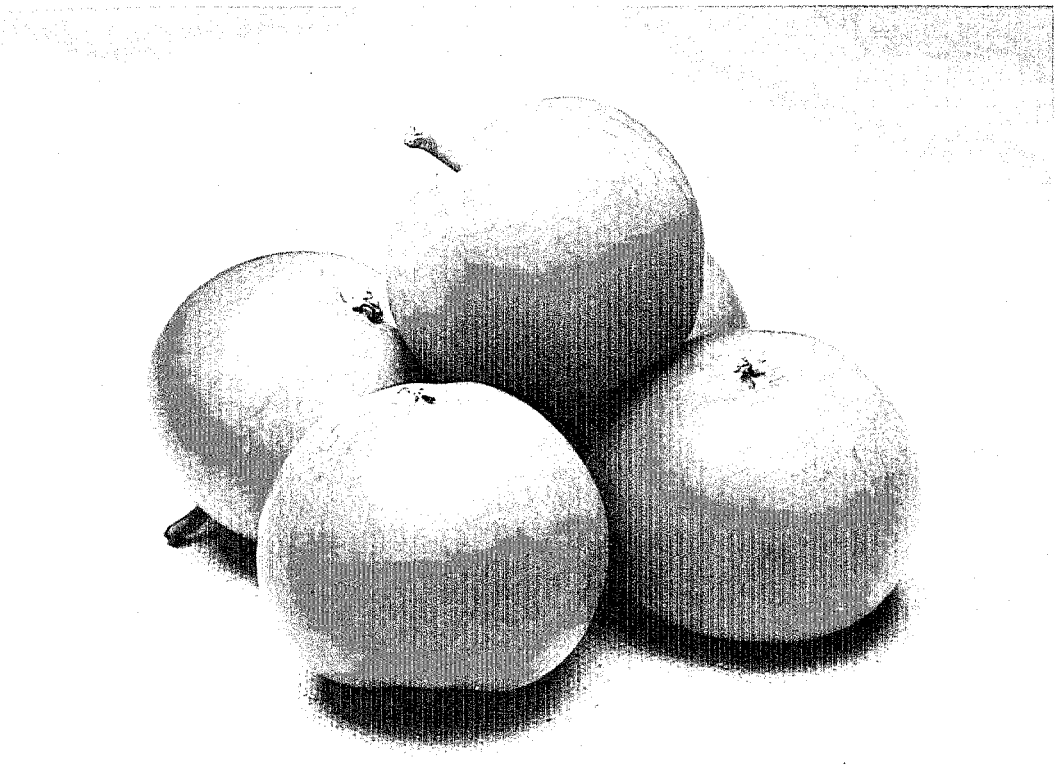

Tree:

*Habit of branches.*—Branches tend to droop (as illustrated in FIG. 1), this characteristic is particularly apparent when young trees are observed, and the branch angles tend to be wide.

*Growth habit.*—When present on MM106 rootstock the tree is approximately twenty-five percent larger than its parent, the Cox's Orange Pippin cultivar, at the age of four years.

*Vigor.*—Strong.

*Dormant one year old shoot.*—Pubescence is only weakly present, there is a medium leader thickness, and the lenticels are present in a moderate quantity.

Leaves:

*Leaf configuration.*—Elongated, and commonly exhibit a length to width ratio of approximately 1.9:1.

*Leaf margin.*—Crenate.

*Leaf appearance.*—Medium glossy (as illustrated).

*Petiole.*—Long, and approximately 28 mm. in length on average.

*Leaf posture.*—Generally outwards.

Flowers:

*Dormant bud shape.*—Ovoid.

*Bud pubescence.*—Medium.

*Bud color.*—Deep pink, Red Group 55A.

*Beginning of flowering.*—Approximately two days later than the Cox's Orange Pippin cultivar when approximately ten percent flowering occurs.

*Flower configuration.*—Moderately uncupped.

*Flower size.*—Medium.

*Sepals.*—Predominantly green in coloration.

*Petal shape.*—Longer than broad, and commonly have a length to breadth ratio of approximately 1.4:1.

*Relation of petal margins.*—Overlapping.

*Styles.*—Slightly longer than the stamens, and tend to be attached away from the base.

Fruit:

*Predominance of bearing.*—On spurs.

*Size.*—Medium, approximately 64 mm. in diameter on average.

*Shape.*—Globose-conical.

*Symmetry in sideview.*—Asymmetric.

*Ribbing.*—Absent.

*Crowning at distal end.*—Present.

*Aperture of eye.*—Closed.

*Size of eye.*—Medium.

*Length of sepal.*—Medium.

*Attitude of sepal.*—Partially reflexed.

*Spacing of sepals at base.*—Touching.

*Ribbing of basin.*—Present.

*Protrusion of stalk.*—Moderately beyond cavity.

*Thickness of stalk.*—Relatively thick.

*Length of stalk.*—Medium to long.

*Stalk cavity depth.*—Medium.

*Surface texture of skin.*—Smooth.

*Bloom of skin.*—Absent.

*Greasiness of skin.*—Absent at harvest time.

*Cracking tendency of skin.*—Absent.

*Skin color.*—Ground color is Yellow-Green Group 150B and the over color is Red Group 46A or Red Group 46B which commonly includes stripes and speckles in its distribution over approximately fifty percent of the fruit surface.

*Russet.*—Absent or weak.

*Position of russet.*—Around the cavity when present.

*Lenticels.*—Small in size.

*Color of flesh.*—Cream to white.

*Browning of flesh.*—Weak.

*Position of stamens.*—Marginal when examined in longitudinal section.

*Shape of core.*—Symmetric when examined in longitudinal section.

*Distinctness of coreline.*—Absent or very weak when examined in cross-section.

*Aperture of cells.*—Closed when examined in cross-section.

*Color of fresh seed.*—Brown.
*Maturity date.*—Mid-season.

I claim:

1. A new and distinct variety of apple tree having the following combination of characteristics:

(a) is precocious and assumes a larger size than the Cox's Orange Pippin cultivar,
(b) exhibits a somewhat drooping growth habit which is particularly noticeable in young trees, (c) forms in good yields attractive round and slightly flattened fruit having a smooth and shiny surface with a bright red blush which may be present as stripes and speckles on a yellow-green background and possessing an excellent flavor which is well retained upon storage, and
(d) commonly exhibits a genetic leaf mottle which is unrelated to disease;

substantially as herein shown and described.

* * * * *